(12) United States Patent
Hartley et al.

(10) Patent No.: US 7,892,275 B2
(45) Date of Patent: Feb. 22, 2011

(54) DOCKING ARRANGEMENT

(75) Inventors: David Ernest Hartley, Subiaco (AU); Krasnodar Ivancev, Lund (SE); Michael Lawrence-Brown, City Beach (AU)

(73) Assignees: William A. Cook Australia Pty. Ltd., Brisbane (AU); William Cook Europe ApS, Bjaeverskov (DK); Cook Incorporated, Bloomington, IN (US)

( * ) Notice: Subject to any disclaimer, the term of this patent is extended or adjusted under 35 U.S.C. 154(b) by 677 days.

(21) Appl. No.: 11/880,804

(22) Filed: Jul. 24, 2007

(65) Prior Publication Data

US 2008/0033354 A1 Feb. 7, 2008

Related U.S. Application Data

(60) Provisional application No. 60/832,865, filed on Jul. 24, 2006.

(51) Int. Cl.
A61F 2/06 (2006.01)
(52) U.S. Cl. .................................... 623/1.11
(58) Field of Classification Search ................ 623/1.18, 623/1.2, 1.23, 1.13, 1.15, 1.24, 1.25; 606/198
See application file for complete search history.

(56) References Cited

U.S. PATENT DOCUMENTS 4,794,928 A * 1/1989 Kletschka .................... 606/194

| 2001/0039388 | A1* | 11/2001 | Korotko et al. | 600/587 |
|---|---|---|---|---|
| 2002/0165554 | A1* | 11/2002 | Dworschak et al. | 606/108 |
| 2003/0105427 | A1* | 6/2003 | Lee et al. | 604/103.04 |
| 2003/0135259 | A1 | 7/2003 | Simso | |
| 2003/0158597 | A1* | 8/2003 | Quiachon et al. | 623/1.23 |
| 2004/0002754 | A1* | 1/2004 | McDermott | 623/1.23 |
| 2004/0049256 | A1 | 3/2004 | Yee | |
| 2004/0097876 | A1* | 5/2004 | Shkolnik | 604/103 |
| 2004/0106974 | A1* | 6/2004 | Greenberg et al. | 623/1.11 |
| 2004/0148000 | A1* | 7/2004 | Bilge | 623/1.11 |
| 2005/0085842 | A1* | 4/2005 | Eversull et al. | 606/191 |
| 2007/0299499 | A1 | 12/2007 | Hartley | |

FOREIGN PATENT DOCUMENTS

| WO | WO01/67993 A2 | 9/2001 |
|---|---|---|
| WO | WO2007/142962 A2 | 12/2007 |
| WO | PCT/US07/016574 | 3/2008 |

* cited by examiner

Primary Examiner—Kevin T Truong
(74) Attorney, Agent, or Firm—Richard J. Godlewski

(57) ABSTRACT

A stent graft introducer has a nose cone dilator (8) and a distally opening capsule (18) on the nose cone dilator, a balloon guide (2, 30) extending into the capsule and affixed therein. Upon completion of deployment of a stent graft, a balloon catheter (96) including an inflatable balloon (98) thereon can be advanced over the balloon guide at least partially into the nose cone whereby the balloon can be inflated therein to provide a smooth transition from the nose cone to a delivery sheath (10) for retraction of the nose cone dilator through the deployed stent graft. The balloon guide can be a separate wire (30).

13 Claims, 5 Drawing Sheets

DOCKING ARRANGEMENT

CROSS-REFERENCE TO RELATED APPLICATIONS

This application claims priority of provisional application Ser. No. 60/832,865, filed Jul. 24, 2006.

TECHNICAL FIELD

This invention relates to a medical device and more particularly to a medical device used for deployment of an intraluminal graft or stent graft.

BACKGROUND OF THE INVENTION

In the deployment of a graft or stent graft into the human or animal body via intraluminal techniques a deployment device is used to introduce the graft and, after the graft has been deployed and expanded within the lumen, the introducer needs to be retracted.

One form of introducer uses a distally facing capsule to encompass an exposed stent of a stent graft during introduction and after the stent graft has been released and the capsule has been removed from the exposed stent, the capsule along with the introducer must withdrawn. The capsule, however, has a distally facing opening and edge and this can engage with stents of the just introduced stent graft and cause problems with dislodging the stent graft from its position on the wall of the lumen. Similarly, an introducer often has a sheath which is used to constrain a stent or stent graft during delivery and is withdrawn from the stent or stent graft to release the stent or stent graft. This sheath has a proximally facing opening and edge and if the sheath is advanced to meet the nose cone then that edge may engage with stents of the just introduced stent graft and cause problems with dislodging the stent graft from its position on the wall of the lumen.

It is the object of this invention to provide an arrangement by which the nose cone can be retracted to the sheath so that introducer as a whole can be retracted without causing such problems.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in a stent graft introducer comprising a nose cone dilator and a distally opening capsule on the nose cone dilator and a balloon guide extending into the capsule and affixed therein whereby upon completion of deployment of a stent graft from the introducer, a balloon catheter including an inflatable balloon thereon can be advanced over the balloon guide at least partially into the nose cone and the balloon be inflated therein to provide a smooth transition from the nose cone to a delivery catheter for retraction of the nose cone dilator through the deployed stent graft.

Preferably the balloon is a non-compliant balloon whereby upon inflation it inflates to a selected size and shape only.

Preferably the introducer further comprises a guide wire catheter extending to and through the nose cone dilator and the balloon guide is the guide wire catheter. Alternatively the balloon guide is a separate guide wire.

In an alternate form the invention resides in a stent graft introducer comprising guide wire catheter, a nose cone dilator on the proximal end of the guide wire catheter, a distally opening capsule on the nose cone dilator, a sheath coaxially around the guide wire catheter and spaced apart therefrom to define an annular sheath lumen therein and a balloon guide extending through the sheath lumen and into the capsule and affixed therein, whereby upon completion of deployment of a stent graft, a balloon catheter including an inflatable balloon thereon can be advanced over the balloon guide at least partially into the nose cone and the balloon be inflated therein and the nose cone dilator and the inflated balloon retracted together such that the inflated balloon docks into the sheath whereby provide a smooth transition from the nose cone to the sheath for retraction of the stent graft introducer through the deployed stent graft.

Preferably the balloon is a non-compliant balloon whereby upon inflation it inflates to a selected size and shape only and is shaped to be substantially the same diameter as the sheath when in an inflated state.

In one embodiment the guide wire catheter is the balloon guide or alternatively the balloon guide is a separate guide wire extending through the sheath lumen.

In an alternate form the invention resides in a stent graft introducer comprising guide wire catheter, a nose cone dilator on the proximal end of the guide wire catheter, a distally opening capsule on the nose cone dilator, a sheath coaxially around the guide wire catheter and spaced apart therefrom to define an annular sheath lumen therein, a balloon guide extending through the sheath lumen into the capsule and affixed therein, a stent graft retained in the sheath lumen distally of the capsule, the stent graft comprising a proximally extending exposed stent and the proximally extending exposed stent being received and retained in the capsule of the nose cone dilator, whereby upon completion of deployment of the stent graft by retraction of the sheath and advancement of the nose cone dilator to remove the capsule from the proximally extending exposed stent, a balloon catheter including an inflatable balloon thereon can be advanced over the balloon guide at least partially into the nose cone whereby the balloon can be inflated therein and the nose cone dilator and the inflated balloon retracted such that the inflated balloon docks into the sheath whereby provide a smooth transition from the nose cone to the sheath for retraction of the stent graft introducer through the deployed stent graft.

Preferably the balloon is a non-compliant balloon whereby upon inflation it inflates to a selected size and shape only and is shaped to be substantially the same diameter as the sheath when in an inflated state.

In one embodiment the guide wire catheter extending is the balloon catheter and during the deployment of the stent graft the balloon catheter including the inflatable balloon is on the guide wire catheter distally of the retained stent graft.

Alternatively the balloon guide is a separate guide wire extending through the sheath lumen and the balloon catheter including the inflatable balloon is introduced onto the balloon guide after deployment of the stent graft. Alternatively the balloon catheter including the inflatable balloon may be carried on the separate guide wire distally of the retained stent graft during introduction.

In an alternate form the invention resides in a stent graft introducer comprising guide wire catheter, a nose cone dilator on the proximal end of the guide wire catheter, a distally opening capsule on the nose cone dilator, a sheath coaxially around the guide wire catheter and spaced apart therefrom to define an annular sheath lumen therein, a stent graft retained in the sheath lumen distally of the capsule, the stent graft comprising a proximally extending exposed stent and the proximally extending exposed stent being received and retained in the capsule of the nose cone dilator, a balloon catheter mounted coaxially onto the guide wire catheter and able to be moved therealong, during deployment the balloon catheter being positioned distally of the stent graft, whereby upon completion of deployment of the stent graft by retraction of the sheath and advancement of the nose cone dilator to remove the capsule from the proximally extending exposed stent, a balloon catheter including an inflatable balloon thereon can be advanced along the guide wire catheter at least partially into the nose cone whereby the balloon can be inflated therein and the nose cone dilator and the inflated balloon retracted such that the inflated balloon docks into the sheath whereby provide a smooth transition from the nose cone to the sheath for retraction of the stent graft introducer through the deployed stent graft.

It will be seen that by this invention there is provided an arrangement by which a balloon can be introduced at least partially into the capsule of an introducer after deployment of the stent graft and the balloon inflated until it is approximately the same diameter as the capsule. During retraction the balloon will act as a fairing to prevent the capsule engaging against the previously introduced stent graft until such time as the capsule is fully retracted or retracted sufficiently into an introducer sheath that the whole device can be withdrawn successfully.

As discussed above the balloon catheter and inflator balloon can be carried on the stent graft introducer distally of a stent graft during the introduction process and advanced when it is required to be used to assist with docking of the capsule.

Alternatively the balloon catheter can be introduced through a hemostatic seal on the introducer over the separate guide wire and advanced into the nose cone and inflated as discussed above.

This then generally describes the invention but to assist with understanding reference will now be made to the accompanying drawings which show in a stylised form preferred embodiments of the invention.

DETAILED DESCRIPTION

FIGS. 1A to 1E show in a stylised manner the operation of a docking balloon arrangement according to one embodiment of the invention.

Figure 1:
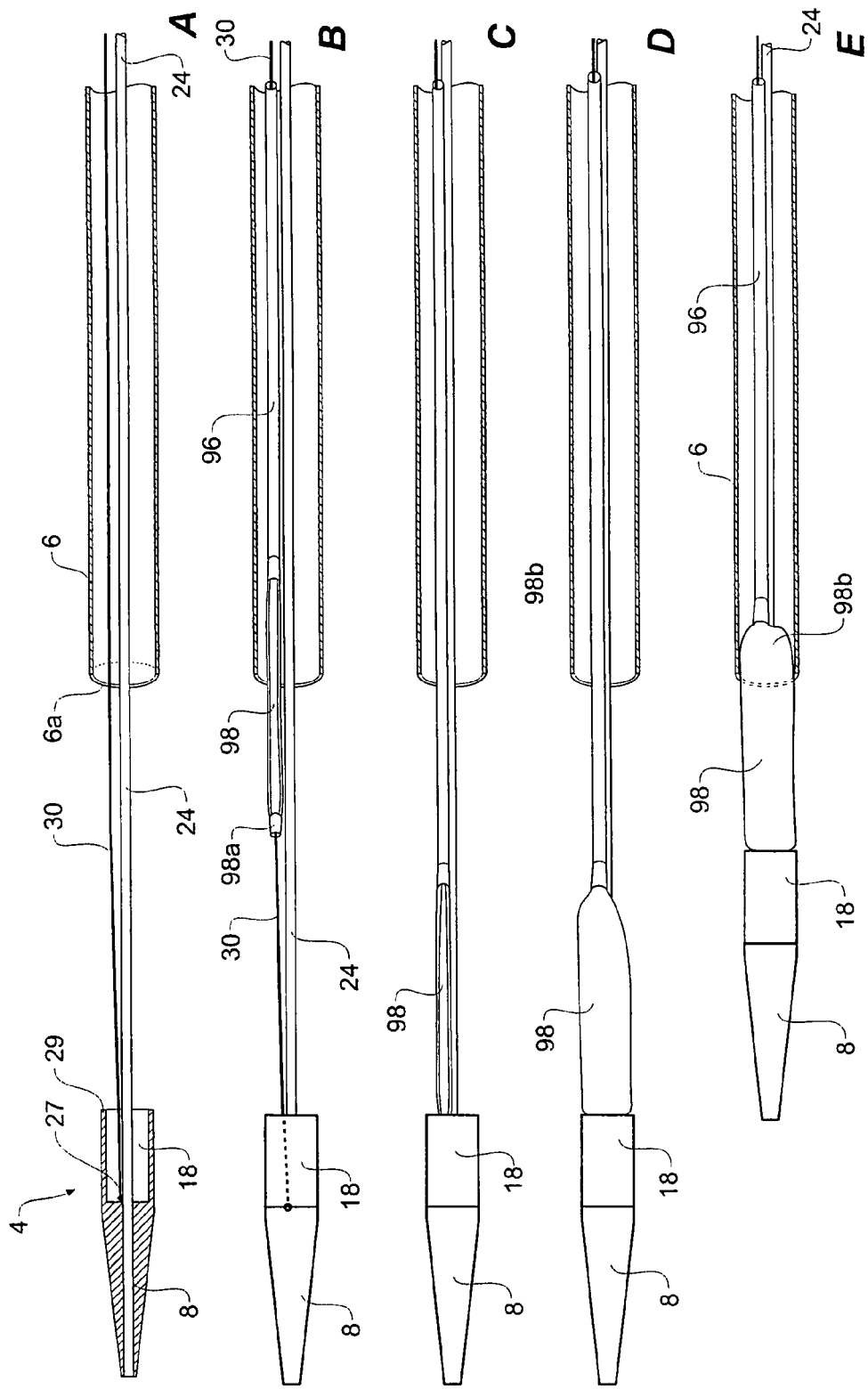
FIGS. 1A to 1E show schematically a first embodiment of the invention.

In this embodiment, as shown in FIG. 1A, the stent graft introducer has a nose cone dilator 8 with a distally facing capsule 18 (shown in section in FIG. 1A) mounted onto a guide wire catheter 24. The guide wire catheter passes through the outer sheath 6. An auxiliary guide wire 30 which extends substantially parallel to the guide wire catheter 24 and extends into the capsule 18 and is fixed inside the capsule and terminates at point 27. The auxiliary guide wire 30 extends through the sheath 6 and haemostatic seal 124 (see FIGS. 3 and 4) of the introducer.

After the stent graft has been deployed, the introducer is as shown in FIG. 1A. At this stage, if the nose cone dilator 8 with capsule 18 is retracted to dock with the sheath 6 to enable their retraction together then the distal edge 29 of the capsule 18 could catch against portions of stents within an introduced stent or stent graft and cause the stent or stent graft to be dislodged. Similarly, if the sheath 6 is advanced so that the sheath docks with the capsule then the leading edge 6a of the sheath 6 could catch against portions of stents within an introduced stent graft and cause the stent graft to be dislodged. It is necessary to have an arrangement for providing a fairing to prevent engagement with the stents of the stent graft.

As shown in FIG. 1B a balloon catheter 96 has been introducer over the auxiliary guide wire 30 through the hemostatic seal (not shown). The balloon catheter 96 includes a inflatable balloon 98.

The balloon catheter 96 and balloon 98 are advanced along the auxiliary guide wire 25 until its proximal end 98a is received within the capsule 18 as shown in FIG. 1C. The balloon 98 is then inflated as shown in FIG. 1D until it is substantially the same diameter as the capsule 18.

The nose cone 8, capsule 18 and balloon 98 can then be retracted until the distal end 98b of the balloon 98 is engaged within the sheath 6 as shown in FIG. 1E and then the entire introducer device can be retracted without potential problems of engagement against stents of an already deployed stent graft. Alternatively the nose cone dilator 8, capsule 18, balloon 98 and guide wire catheter 24 can all be withdrawn leaving the sheath 6 in place.

FIGS. 2A to 2D show an alternative embodiment of docking arrangement according to the present invention.

Figure 2:
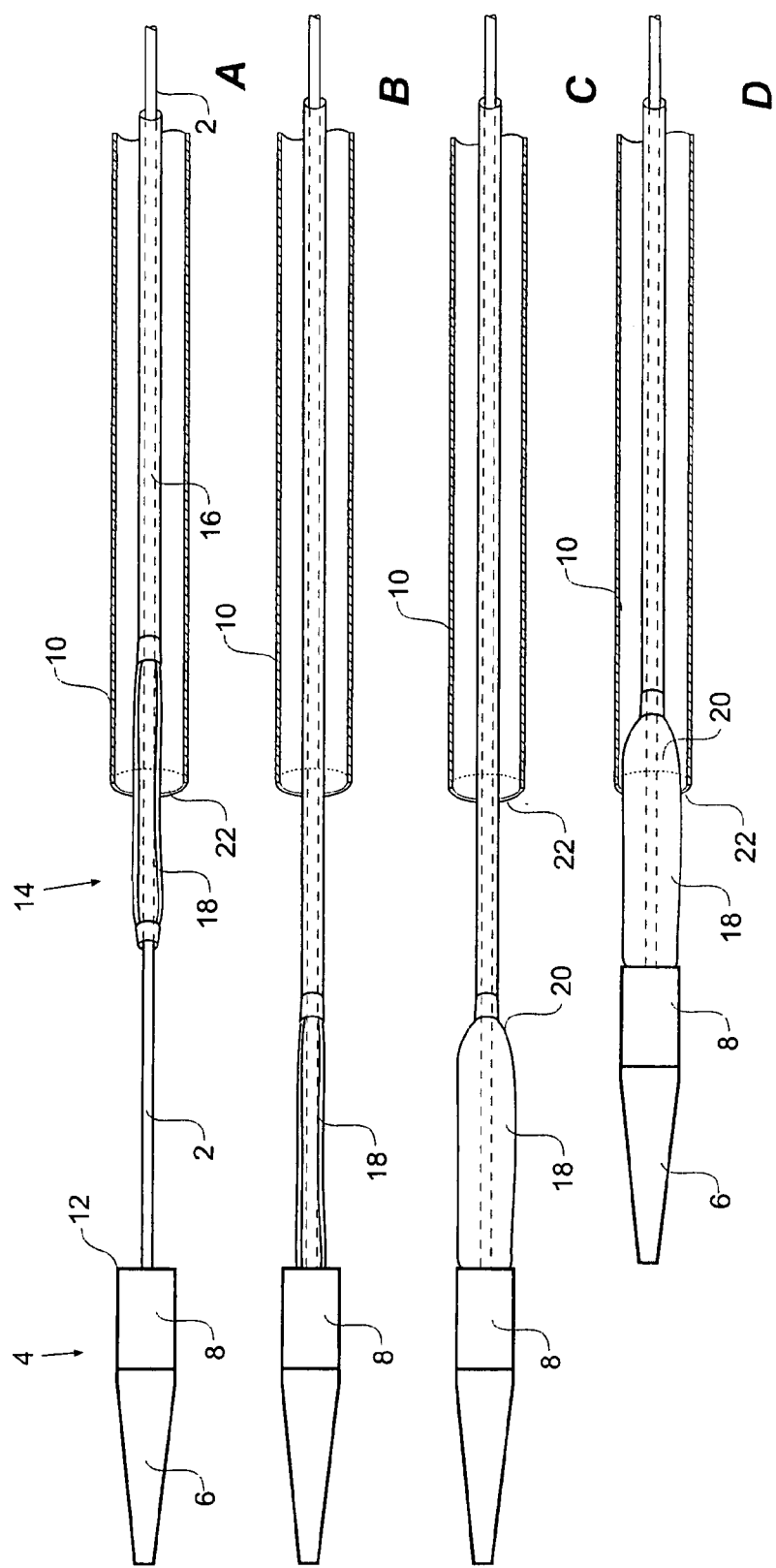
FIGS. 2A to 2D show an alternative embodiment of the invention.

FIG. 2A shows a schematic view of part of a stent graft introducer. The stent graft introducer includes a guide wire catheter 2 which extends from outside the body of a patient in use to a proximal end 4 upon which is mounted a nose cone dilator 6 and a distally facing capsule 8. A sheath 10 surrounds a the guide wire catheter. At the stage shown in FIG. 2A a stent graft (not shown) has been deployed and the introducer is ready to be withdrawn.

At this stage, if the nose cone dilator 6 with capsule 8 is retracted to dock with the sheath 10 to enable their retraction together then the distal edge 12 of the capsule 8 could catch against portions of stents within an introduced stent or stent graft and cause the stent or stent graft to be dislodged. Similarly, if the sheath 10 is advanced so that the sheath docks with the capsule then the leading edge 22 of the sheath 10 could catch against portions of stents within an introduced stent graft and cause the stent graft to be dislodged. It is necessary to have an arrangement for providing a fairing to prevent engagement with the stents of the stent graft.

According to this embodiment of the invention, therefore, a balloon catheter 14 including an elongate catheter 16 and an inflatable balloon 18 is advanced over the guide wire catheter until, as shown in FIG. 2B, the proximal end of the inflatable balloon 18 is received into the capsule 8. The balloon 18 is formed from a non-compliant material such that when inflated it forms a selected size and shape and will not normally expand beyond that size. The desired size and shape is approximately sausage shape with a diameter approximately the same as the capsule on the nose cone dilator.

FIG. 2C shows the balloon 18 inflated until it is substantially the same size as the outer diameter of the capsule 8. At this stage the balloon 18 presents a rounded distal end 20 which will not engage deleteriously with the stents of a stent graft.

The balloon catheter, balloon nose cone dilator and capsule can then be withdrawn until the distal end 20 of the balloon 18 is received in the proximal end 22 of the sheath 10 as shown in FIG. 2D.

At this stage if it is desired to leave the sheath 10 in place for subsequent deployment of stent grafts through the sheath the balloon 18, capsule 8 and nose cone 6 can be withdrawn through the sheath or alternatively the sheath as well can be withdrawn to completely retract the introducer and its components from the vessel of the human or animal body.

Figure 3:
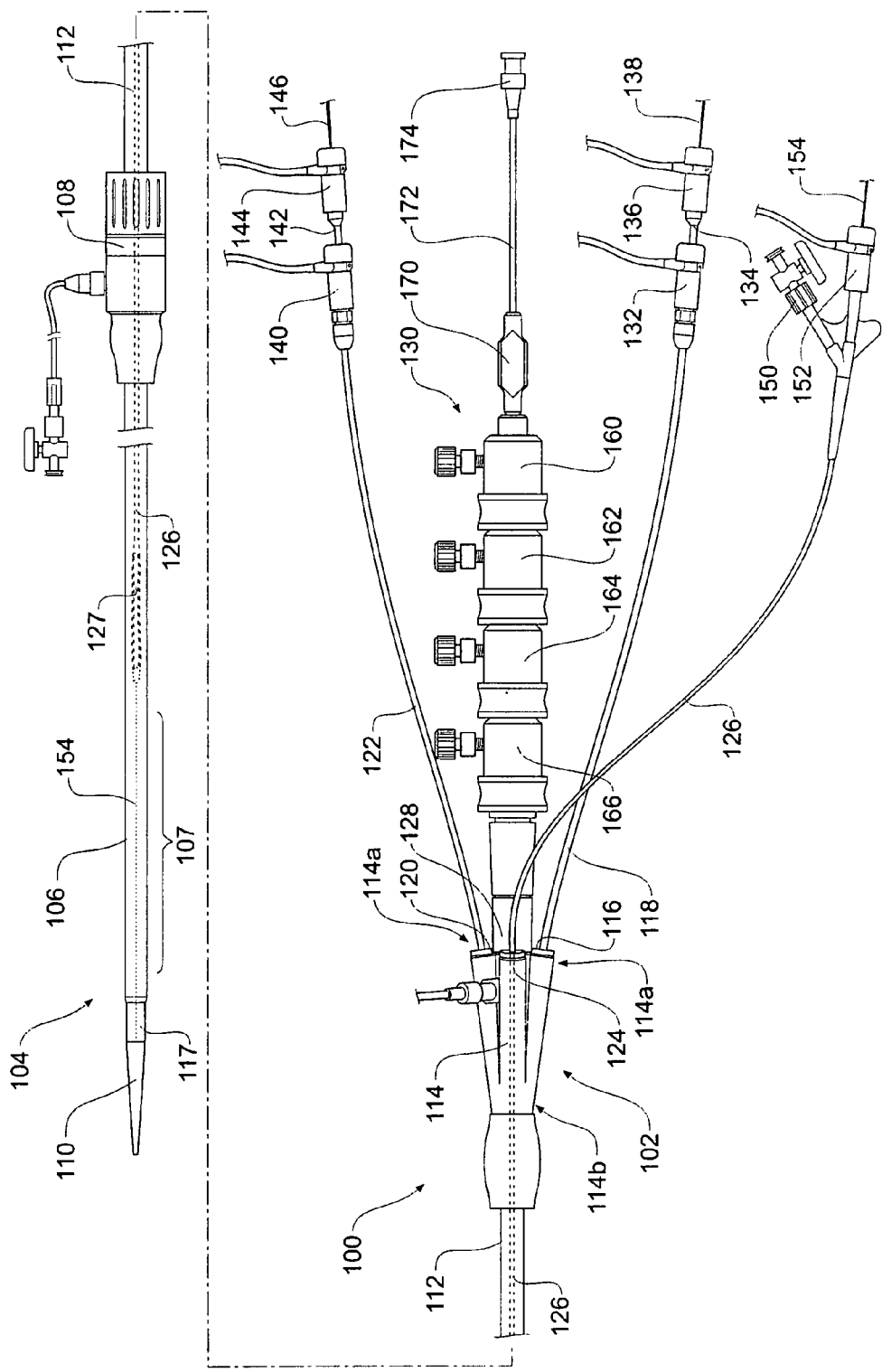
FIG. 3 shows one embodiment of stent graft introducer incorporating a docking balloon arrangement according to the present invention.
Figure 4:
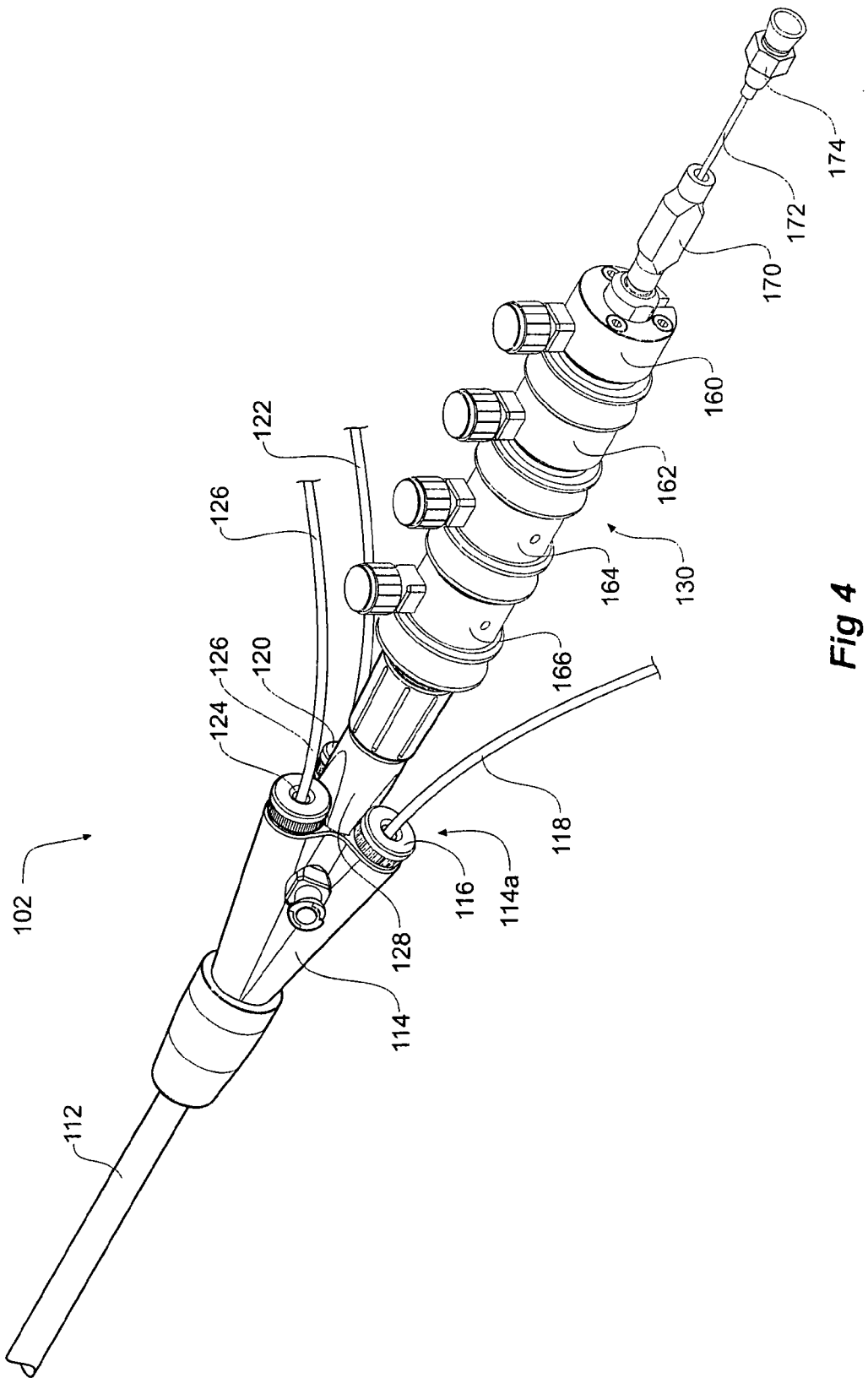
FIG. 4 shows detail of the handle and manifold section of the embodiment shown in FIG. 3.

FIG. 3 shows an alternative embodiment of a multi port stent graft introducer incorporating a docking balloon arrangement according to the present invention. FIG. 4 shows in more detail the manifold and handle portion 102 of the delivery device shown in FIG. 3.

The introducer device 100 shown in FIG. 3 comprises a handle and manifold assembly 102 and introduction portion 104 intended to be deployed into the patient. The introduction section 104 includes an outer sheath 106 extending from an outer sheath manipulator 108 to a nose cone dilator 110. A stent graft is retained within the outer sheath 106 in the region 107 just distal of the nose cone dilator 110.

The outer sheath manipulator 108 is positioned over an inner sheath 112 which extends back and is fastened to the manifold 114. The inner sheath 112 extends proximal at least to a forward most position of the outer sheath manipulator 108 and preferably within the outer sheath to just distal of the stent graft retained within the outer sheath 106. The manifold 114 has a proximal end 114b to which is connected the outer sheath 112 and four access ports at its distal end 114a. Access port 116 is for a first access sheath 118. Access port 120 is for a second access sheath 122. A third access port 124 is for a docking balloon catheter 126.

A fourth port 128 provides access to the handle 130 which includes trigger wire release mechanisms as discussed below.

The access sheath 118 extends to a haemostatic seal 132 through which extends the dilator 134. On the dilator 134 is a dilator haemostatic seal 136 through which extends an indwelling guide wire 138.

The access sheath 122 extends to a haemostatic seal 140 through which extends the dilator 142. On the dilator 142 is a dilator haemostatic seal 144 through which extends an indwelling guide wire 146.

The use of access sheaths 118 and 122 is discussed in co-pending U.S. patent application entitled "Multiport Delivery Device" (Ser. No. 11/807,878 filed May 30, 2007) the teaching of which is incorporated herein in its entirety.

The auxiliary balloon guide wire 154 extends through the balloon catheter haemostatic seal 152 and the inner and outer sheaths 112 and 106 proximally to the nose cone dilator 110 and is fastened to the nose cone dilator 110 within the capsule 117. The balloon catheter 126 extends through balloon catheter haemostatic seal 124 and the inner and outer sheaths 112 and 106 proximally to just distal of the region 107 where the stent graft is carried. The balloon catheter has a non-compliant balloon 127 at its proximal end. The balloon catheter 126 includes an inflation lumen (not-shown) through which inflation medium can be supplied to the balloon 127 via inflation port 150.

The handle assembly 130 includes trigger wire release mechanisms as follows. Trigger wire release 162 is for the diameter reducing ties on a stent graft carried on the delivery device, trigger wire release 160 is for the guide wire retention release wire (not shown). Trigger wire release 164 is for the retention trigger wire for a stent graft exposed stent in a distally facing capsule on the nose cone dilator 110. Trigger wire release mechanism 166 is for the distal end of the stent graft.

A pin vice 170 is at the rear of the handle 130 and the guide wire catheter 172 for the introducer device extends through the pin vice 170 and is locked for movement with respect to the handle 130 by the pin vice. The guide wire catheter 172 terminates in a syringe point 174 to enable flushing liquid and radiopaque medium to be deployed through the delivery device.

Figure 5:
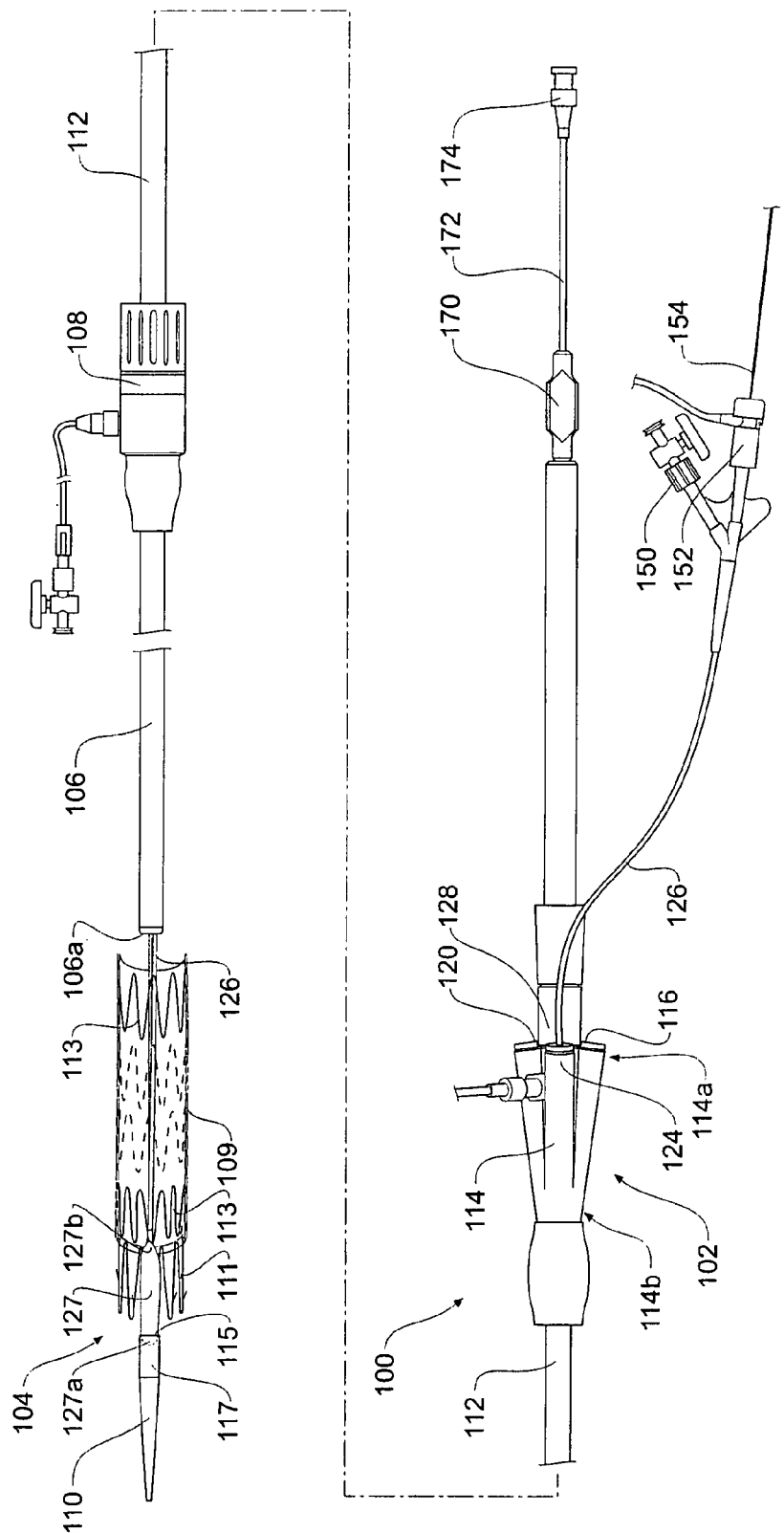
FIG. 5 shows the embodiment of FIG. 3 after release of a stent graft and partial deployment of the docking balloon.

FIG. 5 shows the delivery device of FIGS. 3 and 4 after delivery of a stent graft and before retraction of the nose cone dilator. The vasculature into which the stent graft has been delivered is not shown for reasons of clarity. At this stage each of the access sheaths 118 and 122 (see FIG. 3) have been withdrawn and the trigger wire release mechanisms 162, 160, 164 and 166 (see FIG. 3) have also been withdrawn. Also at this stage the stent graft 109 would be engaged against the wall of the vessel into which it has been deployed but the exposed stent 111 and the internal stents 113 could be engaged by the either the distal edge 115 of the capsule 117 if that was retracted to the sheath or the proximal edge 106a of the outer sheath 106 if that was advanced to the capsule.

FIG. 5 shows that the balloon catheter 126 has been advanced over the guide wire 154 until the proximal end 127a of the balloon 127 has been received in the capsule 117 and the balloon has been inflated until it is approximately the same diameter as the nose cone dilator 117 and the outer sheath 106.

The nose cone dilator 117, the balloon 127 and balloon catheter 126 can then all be withdrawn together until the distal end 127b of the balloon 127 is received in the proximal end 106a of the outer sheath 106. Then either the entire delivery device 100 can be withdrawn or the nose cone dilator 117, the balloon 127 and balloon catheter 126 can then all be withdrawn together until they are received in the inner sheath 112 and then these along with the handle assembly 102 can be withdrawn leaving the outer sheath 106 in place for subsequent endovascular procedures therethrough.

Throughout this specification various embodiments of the invention have been discussed but the invention is not limited to any one of them but may reside in two or more combined together in part or in whole. The examples are given for illustration only and not for limitation.

What is claimed is:

1. A stent graft introducer comprising a proximal end and a distal end, the proximal end being able to be deployed into a patient to deploy a stent graft therein, a nose cone dilator at the proximal end of the stent graft introducer and a distally opening capsule on the nose cone dilator and a balloon guide extending into the capsule and affixed therein, a balloon catheter including an inflatable balloon at the proximal end of the balloon catheter, the balloon catheter being on the balloon guide, the balloon catheter being able to be advanced with respect to the nose cone dilator on the balloon guide such that the inflatable balloon is moved from a position away from the nose cone dilator to a position in which it is at least partially into the capsule in the nose cone dilator whereby upon completion of deployment of a stent graft, the balloon catheter and inflatable balloon thereon can be advanced over the balloon guide such that the inflatable balloon is at least partially into the nose cone and the balloon inflated therein to provide a smooth transition from the nose cone to a delivery sheath for retraction of the nose cone dilator through the deployed stent graft.

2. A stent graft introducer as in claim 1 wherein the balloon is a non-compliant balloon whereby upon inflation it inflates to a selected size and shape only.

3. A stent graft introducer as in claim 1 wherein the introducer further comprises a guide wire catheter extending to and through the nose cone dilator and the guide wire catheter comprises the balloon guide.

4. A stent graft introducer as in claim 1 wherein the balloon guide is a separate guide wire.

5. A stent graft introducer comprising a guide wire catheter, a nose cone dilator on the proximal end of the guide wire catheter, a distally opening capsule on the nose cone dilator, a sheath coaxially around the guide wire catheter and spaced apart therefrom to define an annular sheath lumen therein and a balloon guide extending through the sheath lumen into the capsule and affixed therein, a balloon catheter including an inflatable balloon at the proximal end of the balloon catheter, the balloon catheter being on the balloon guide, the balloon catheter being able to be advanced with respect to the nose cone dilator on the balloon guide such that the inflatable balloon is moved from a position away from the nose cone dilator to a position in which it is at least partially into the capsule in the nose cone dilator whereby upon completion of deployment of a stent graft, the balloon catheter and inflatable balloon thereon can be advanced over the balloon guide such that the inflatable balloon is at least partially into the nose cone and the balloon inflated therein and the nose cone dilator and the inflated balloon retracted such that the inflated balloon docks into the sheath whereby provide a smooth transition from the nose cone to the sheath for retraction of the stent graft introducer through the deployed stent graft.

6. A stent graft introducer as in claim 5 wherein the balloon is a non-compliant balloon whereby upon inflation it inflates to a selected size and shape only and is shaped to be substantially the same diameter as the sheath when in an inflated state.

7. A stent graft introducer as in claim 5 wherein the guide wire catheter comprises the balloon guide.

8. A stent graft introducer as in claim 5 wherein the balloon guide is a separate guide wire extending through the sheath lumen.

9. A stent graft introducer comprising a guide wire catheter, a nose cone dilator on the proximal end of the guide wire catheter, a distally opening capsule on the nose cone dilator, a sheath coaxially around the guide wire catheter and spaced apart therefrom to define an annular sheath lumen therein, a balloon guide extending through the sheath lumen into the capsule and affixed therein, a balloon catheter including an inflatable balloon at the proximal end of the balloon catheter, the balloon catheter being on the balloon guide, the balloon catheter being able to be advanced with respect to the nose cone dilator on the balloon guide such that the inflatable balloon is moved from a position away from the nose cone dilator to a position in which it is at least partially into the capsule in the nose cone dilator, a stent graft retained in the sheath lumen distally of the capsule, the stent graft comprising a proximally extending exposed stent and the proximally extending exposed stent being received and retained in the capsule of the nose cone dilator, whereby upon completion of deployment of the stent graft by retraction of the sheath and advancement of the nose cone dilator to remove the capsule from the proximally extending exposed stent, the balloon catheter and inflatable balloon thereon can be advanced over the balloon guide such that the inflatable balloon is at least partially into the nose cone and the balloon inflated therein and the nose cone dilator and the inflated balloon retracted such that the inflated balloon docks into the sheath whereby provide a smooth transition from the nose cone to the sheath for retraction of the stent graft introducer through the deployed stent graft.

10. A stent graft introducer as in claim 9 wherein the balloon is a non-compliant balloon whereby upon inflation it inflates to a selected size and shape only and is shaped to be substantially the same diameter as the sheath when in an inflated state.

11. A stent graft introducer as in claim 9 wherein the guide wire catheter extending is the balloon catheter and during the deployment of the stent graft the balloon catheter including the inflatable balloon is on the guide wire catheter distally of the retained stent graft.

12. A stent graft introducer as in claim 9 wherein the balloon guide is a separate balloon guide wire extending through the sheath lumen and the balloon catheter including the inflatable balloon is introduced onto the balloon guide wire after deployment of the stent graft.

13. A stent graft introducer comprising a guide wire catheter, a nose cone dilator on the proximal end of the guide wire catheter, a distally opening capsule on the nose cone dilator, a sheath coaxially around the guide wire catheter and spaced apart therefrom to define an annular sheath lumen therein, a stent graft retained in the sheath lumen distally of the capsule, the stent graft comprising a proximally extending exposed stent and the proximally extending exposed stent being received and retained in the capsule of the nose cone dilator, a balloon catheter mounted coaxially onto the guide wire catheter and able to be moved therealong, during deployment the balloon catheter being positioned distally of the stent graft, the balloon catheter including an inflatable balloon at a proximal end thereof, the balloon catheter being able to be advanced with respect to the nose cone dilator on the guide wire catheter such that the inflatable balloon is moved from a position away from the nose cone dilator to a position in which it is at least partially into the capsule in the nose cone dilator, the balloon comprising a non-compliant balloon being shaped to be substantially the same diameter as the sheath when in an inflated state whereby upon inflation it inflates to a selected size and shape only whereby upon completion of deployment of the stent graft by retraction of the sheath and advancement of the nose cone dilator to remove the capsule from the proximally extending exposed stent, the balloon catheter including the inflatable balloon thereon can be advanced along the guide wire catheter such that the inflatable balloon is at least partially into the nose cone and the balloon inflated therein and the nose cone dilator and the inflated balloon retracted together such that the inflated balloon docks into the sheath thereby providing a smooth transition from the nose cone to the sheath for retraction of the stent graft introducer through the deployed stent graft.

* * * * *